United States Patent [19]

Glandorf et al.

[11] Patent Number: 4,849,212
[45] Date of Patent: Jul. 18, 1989

[54] PEARLESCENT DENTIFRICE COMPOSITIONS

[75] Inventors: William M. Glandorf; Jane R. Camplejohn, both of Cincinnati; Thomas E. Huetter, West Chester, all of Ohio

[73] Assignee: The Procter & Gamble Company, Cincinnati, Ohio

[21] Appl. No.: 64,895

[22] Filed: Jun. 22, 1987

Related U.S. Application Data

[63] Continuation-in-part of Ser. No. 921,167, Oct. 20, 1986, abandoned.

[51] Int. Cl.$^4$ .......................... A61K 7/18; A61K 7/16
[52] U.S. Cl. ........................................ 424/52; 424/49
[58] Field of Search ....................... 424/49, 52, 55, 57, 424/58

[56] References Cited

U.S. PATENT DOCUMENTS

| | | | |
|---|---|---|---|
| 3,711,604 | 1/1973 | Colodney et al. | 424/52 |
| 3,944,661 | 3/1976 | Colodney et al. | 424/49 |
| 3,954,961 | 5/1976 | Colodney et al. | 424/49 |

FOREIGN PATENT DOCUMENTS

| | | |
|---|---|---|
| 982946 | 2/1976 | Canada . |
| 1309209 | 3/1973 | United Kingdom . |
| 1414678 | 11/1975 | United Kingdom . |

*Primary Examiner*—Howard E. Schain
*Assistant Examiner*—F. T. Moezie
*Attorney, Agent, or Firm*—Richard C. Witte; Jack D. Schaeffer; Douglas C. Mohl

[57] ABSTRACT

Dentifrice compositions are disclosed which have an improved pearlescence.

8 Claims, No Drawings

PEARLESCENT DENTIFRICE COMPOSITIONS

CROSS REFERENCE TO RELATED APPLICATION

This is a continuation-in-part application of our co-pending application Ser. No. 921,167 filed Oct. 20, 1986, now abandoned.

TECHNICAL FIELD

The present invention relates to dentifrices which have improved pearlescence due to the inclusion of pearlescent particles having optimal particle size.

BACKGROUND OF THE INVENTION

The use of transparent or translucent dentifrices has found good acceptance particularly among children. The clear character has visual appeal and encourages use of the product among the target user group.

Since transparent or translucent dentifrices are appealing to particular users, attempts have been made to improve their appearance even more as well as the appearance of opaque pastes. Several attempts at making dentifrices containing irridescent or pearlescent flakes are disclosed in the patent literature. Included among such patents is British Pat. No. 1 309 209, March, 1973 to Colgate-Palmolive disclosing mother of pearl and coated mica particles in toothpastes. U.S. Pat. No. 3,711,604, Jan. 16, 1973 to Colodney et al. discloses speckles containing stannous fluoride dispersed in a clear dentifrice. U.S. Pat. No. 3,954,961, May 4, 1976 to Colodney et al. discloses dentifrices containing flakes of alpha-alumina and irridescent flakes such as titanium dioxide coated mica. U.S. Pat. No. 3,944,661, Mar. 16, 1976 to Colodney et al. discloses dentifrices containing mother of pearl or other irridescent material.

Another patent disclosing pearlescent products is Canadian Pat. No. 982,946, Feb. 3, 1976 to Pader, et al. (incorporated herein by reference). This patent discloses dentifrice compositions containing mother of pearl flakes or mica flakes coated with a thin layer of titanium dioxide. The particle size of the particles is less than about 590 microns with the mother of pearl flakes preferably being from 150 to 590 microns and the mica flakes being less than 100 microns.

The present inventors have surprisingly found that if the particle size is maintained within a very specific range, improved product acceptance is obtained.

It is an object, therefore, of the present invention to provide dentifrice compositions having improved pearlescence.

It is a further object of the present invention to provide clear dentifrice products having improved pearlescence.

It is a further object of the present invention to provide dentifrice compositions which not only have improved pearlescence but also have good cleaning.

It is still a further object of the present invention to provide dentifrice compositions which have improved pearlescence, good cleaning and provide fluoride protection.

These and other objects will become more apparent from the detailed disclosure given below. All percentages and ratios herein are by weight unless otherwise specified.

SUMMARY OF THE INVENTION

The present invention embraces dentifrice compositions comprising pearlescent particles in a suitable dentifrice base wherein at least about 60% of the particles are larger than about 60 microns and wherein at least about 10% of the particles are in the range of from about 100 microns to about 200 microns.

It is found that larger particles, particularly those in the 100–200 micron range, provide sparkle while maintaining gel clarity. Good gel clarity allows the observation of particles inside a given volume of dentifrice and not just on the surface, thereby increasing total sparkle. Moreover, it is found that smaller particles, particularly those smaller than about 60 microns, do not themselves provide substantial sparkle and also tend to opacify the gel, resulting in less total sparkle of the dentifrice.

DETAILED DESCRIPTION OF THE INVENTION

The compositions of the present invention comprise pearlescent particles in a suitable dentifrice base.

By "safe and effective amount", as used herein, means sufficient amount to provide the intended function while being safe to the hard soft tissues of the oral cavity.

By the term "comprising" as used herein, is meant that various additional components can be cojointly employed in the compositions of the invention so long as the pearlescent material can perform its intended function.

By "suitable dentifrice base" as used herein, is meant a base which will allow the pearlescent material to perform its intended function.

PEARLESCENT PARTICLE

The materials which impart sparkle, iridescence or pearlescence to dentifrices are generally particulate and have a plate-like structure. The materials are generally translucent and have a refractive index which is different from that of the bulk dentifrice.

Among the pearlescent materials found useful in the present invention are mother of pearl flakes and mica flakes which have been coated with a thin layer of titanium dioxide. One type of such flakes comprises mica platelets having a $TiO_2$ content of about 20%, an average thickness of less than about 1 micron and a particle size wherein at least about 60% of the particles are greater than about 60 microns and at least about 10% of the particles are in the range of from about 100 microns to about 200 microns.

The mother of pearl flakes typically are flat and smooth surface. These flakes also have a particle size (as defined above) similar to that for the mica particles.

The pearlescent material is used in the present compositions at a level of from about 0.01% to about 0.50%, preferably from about 0.05% to about 0.15%.

SUITABLE DENTIFRICE BASE

The dentifrice base useful with the pearlescent particles in the present invention can be any suitable base which will allow the pearlescent material to provide its pearlescent benefit. Preferred bases are either transparent or translucent.

Dentifrices generally contain an abrasive material to aid in cleaning of the teeth. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insolule sodium polymetaphosphate, hydrated alumina, and resinuous abrasive materials such as particulate condensaiton products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasives, generally have an average particle size ranging between about 0.1 to 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. HUber Corporation under the tradename, "Zeodent", particularly the silica carrying the designation "Zeodent 119". These silica abrasives are described in U.S. Pat. No. 4,340,583, July 29, 1982, incorporated herein by reference. Since preferred dentifrice bases of the preferred invention are translucent or transparent, silicas are ideally suitable since their refractive indices are close to those of the solvents in the dentifrice.

The abrasive in the dentifrice compositions described herein is present at a level of from about 6% to about 70%, preferably from about 15% to about 25%.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonalby stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977, incorporated by reference.

It is common to have a water-soluble fluoride compound present in dentifrices in an amount sufficient to give a fluoride concentration of from about 0.0025% to about 5.0% by weight, preferably from about 0.005% to about 2.0% by weight, to provide additional anticaries effectiveness. Preferred fluorides are sodium fluoride, stannous fluoride, indium fluoride, and sodium monofluorophosphate. Norris et al., U.S. Pat. No. 2,946,735, isued July 26, 1960 and Widder et al., U.S. Pat. No. 3,678,154, issued July 18, 1972 disclose such salts as well as others. Both patents are incorporated herein by reference.

Therapeutic agents other than fluoride may also be incorporated into the compositions of the present invention. Included are anticalculus agents such as soluble pyrophosphate salts as disclosed in U.S. Pat. No. 4,515,772, May 7, 1985 to Parran, et al.; polyphosphates as disclosed in U.S. Pat. No. 3,678,154, July 18, 1972 to Widder et al.; and polyacrylic acid as disclosed in U.S. Pat. No. 3,429,963, Feb. 25, 1969 to Shedlovsky. All of these patents are incorporated herein by reference.

Other preferred agents are antimicrobial agents to reduce plaque and gingivitis. Preferred agents are quaternary ammonium compounds and substituted guanidines such as chlorhexidine and alexidine. Agents of these types are disclosed in U.S. Pat. No. 3,937,807, Feb. 10, 1976 to Haefele; U.S. Pat. No. 4,256,731, Mar. 17, 1981 to Curtis et al.; and U.S. Pat. No. 4,169,885, Oct. 2, 1979, to Raaf et al. all incorporated herein by reference.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with Sorbitol.

In preparing toothpastes, it is necessary to add some thickening material to provide desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, xanthan gum and gum tragacanth can also be sed. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to 60%.

METHOD OF MANUFACTURE

The dentifrices of the present invention can be made using processes which are conventional in the oral hygiene area. It is preferred, however, to add the pearlescent agents to the liquid components along with other solids except for the binder materials which are added later. This procedure allows for easier mixing while still allowing for the binders to function properly.

PRODUCT USAGE

The compositions of the present invention are used in a conventional method. Amounts of the compositions used are not critical and may be any amount commonly used with such products.

The following examples further describe and demonstrate the preferred embodiments within the scope of the present invention. The examples are given solely for illustration and are not to be construed as limitations of this invention as many variations thereof are possible without departing from the spirit and scope thereof.

EXAMPLE I

The following composition is representative of the present invention.

| Component | Level |
| --- | --- |
| Sorbitol (70% solution) | 60.467 |
| Double Reverse Osmosis Water | 10.980 |
| Sodium Fluoride | 0.243 |
| Sodium Saccharin | 0.320 |
| Trisodium Phosphate | 1.450 |
| Monosodium Phosphate | 0.590 |
| Dye | 0.500 |
| Silica | 20.000 |
| Xanthan gum | 0.500 |
| Carbopol | 0.250 |
| Sodium alkyl sulfate | 4.000 |
| Flavor | 0.600 |
| Mica[1] | 0.100 |
| | 100.000 |

EXAMPLE II

| Component | Level |
| --- | --- |
| Sorbitol (70% solution) | 60.467 |
| Double Reverse Osmosis Water | 11.030 |
| Sodium Fluoride | 0.243 |
| Sodium Saccharin | 0.320 |
| Trisodium Phosphate | 1.450 |
| Monosodium Phosphate | 0.590 |
| Dye | 0.500 |
| Silica | 20.000 |
| Xanthan gum | 0.500 |
| Carbopol | 0.250 |
| Sodium alkyl sulfate | 4.000 |
| Flavor | 0.600 |
| Mica[1] | 0.050 |
| | 100.000 |

EXAMPLE III

The following composition is representative of the present invention.

| Component | Level |
| --- | --- |
| Sorbitol (70% solution) | 60.467 |
| Double Reverse Osmosis Water | 10.980 |
| Sodium Fluoride | 0.243 |
| Sodium Saccharin | 0.320 |
| Trisodium Phosphate | 1.450 |
| Monosodium Phosphate | 0.590 |
| Dye | 0.500 |
| Silica | 20.000 |
| Xanthan gum | 0.500 |
| Carbopol | 0.250 |
| Sodium alkyl sulfate | 4.000 |
| Flavor | 0.600 |
| Mica[2] | 0.100 |
| | 100.000 |

[1] The mica particles have a titanium dioxide coating and a particle size distribution wherein at least 60% of the particles are greater than 60 microns with at least 10% of the particles in the range of from 100 to 150 microns.
[2] The mica particles have a titanium dioxide coating and a particle size distribution wherein at least 60% of the particles are greater than 60 microns with at least 10% of the particles in the range of 150 microns to 200 microns.

The particle size measurements are made using a GE Tyler RO-TAP® Testing Sieve Shaker, Model B. Used with this device are U.S.A. Standard Testing Sieves, ASTM E-11, AASHO M92, U.S.A. Standard Z23.1 and Federal Specification RR-S-366b Compliance, which are eight inch Diameter Stainless Steel Sieves. The U.S. Series Sieve Designation and corresponding Tyler Equivalent Designation for these sieves are:

| U.S. Series Sieve Designation (Standard) | Tyler Equivalent Designation |
| --- | --- |
| 177 micron | 80 mesh |
| 150 | 100 |
| 125 | 115 |
| 106 | 150 |
| 90 | 170 |
| 75 | 200 |
| 63 | 250 |

The screens are stacked on the RO-TAP in ascending micron size; 63 μm on the bottom to 177 μm on top. A 200 g sample is placed on the 177 μm (80 mesh) screen. The RO-TAP is set at 30 minutes running time. Each screen is removed and cleaned separately with each fraction being labeled and weighed.

All of the above compositions have excellent pearlescence. The mica levels can be varied within the range set forth herein with similar performance obtained. Also, if mother of pearl particles having the appropriate particle size are used, similar performance is achieved.

What is claimed is:

1. A dentifrice composition comprising from about 0.01% to about 0.50% of non-toxic pearlescent particles of titanium dioxide coated mica in an acceptable dentifrice base wherein at least about 60% of the particles are larger than about 60 microns and wherein at least about 10% of the particles are in the range of from about 100 microns to about 200 microns.

2. A dentifrice composition according to claim 1 wherein the dentifrice base is translucent or transparent.

3. A dentifrice composition according to claim 2 wherein thre dentifrice base contains a silica abrasive.

4. A dentifrice composition according to claim 3 which also contains a soluble fluoride source.

5. A dentifrice composition according to claim 4 wherein the soluble fluoride ion source is sodium fluoride.

6. A dentifrice composition according to claim 5 which in addition contains an agent selected from the group consisting of flavoring agents, emulsifying agents, water, thickening agents, humectants and mixtures thereof.

7. A dentifrice composition according to claim 1 which in addition contains an anticalculus agent.

8. A dentifrice composition according to claim 1 which in addition contains an antiplaque or antigingivitis agent.

* * * * *

UNITED STATES PATENT OFFICE
CERTIFICATE OF CORRECTION

PATENT NO. : 4,849,212
DATED : July 18, 1989
INVENTOR(S) : William M. Glandorf, Jane R. Camplejohn, Thomas E. Huetter It is certified that error appears in the above-identified patent and that said Letters Patent is hereby corrected as shown below:

Column 2, line 25, "hard soft tissues" should read --hard and soft tissues--.

Column 2, line 53, "smooth surface." should read --smooth surfaced.--.

Column 3, line 4, "insolule" should read --insoluble--.

Column 3, line 6, "condensai-ton" should read --condensa-tion--.

Column 3, line 29, "J. M. HUber" should read --J. M. Huber--.

Column 4, line 36, "also be sed." should read --also be used.--.

Column 4, line 47, "60%" should read --70%--.

Column 5, line 52, "wherein thre" should read --wherein the--.

Signed and Sealed this

Eighteenth Day of September, 1990

Attest:

HARRY F. MANBECK, JR.

*Attesting Officer*      *Commissioner of Patents and Trademarks*